(12) United States Patent
Paesch et al.

(10) Patent No.: US 11,478,294 B2
(45) Date of Patent: Oct. 25, 2022

(54) MEDICAL INSTRUMENT

(71) Applicant: Erbe Elektromedizin GmbH, Tuebingen (DE)

(72) Inventors: Markus Paesch, Albstadt (DE); Volker Buntrock, Reutlingen (DE); David Loeser, Rottenburg am Neckar (DE); Stefanie Schmidt, Pliezhausen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 405 days.

(21) Appl. No.: 16/553,769

(22) Filed: Aug. 28, 2019

(65) Prior Publication Data

US 2020/0069362 A1    Mar. 5, 2020

(30) Foreign Application Priority Data

Aug. 29, 2018   (EP) .................................... 18191442

(51) Int. Cl.
*A61B 18/14* (2006.01)
*A61B 17/28* (2006.01)
(Continued)

(52) U.S. Cl.
CPC ...... *A61B 18/1445* (2013.01); *A61B 17/2841* (2013.01); *A61B 2017/00367* (2013.01);
(Continued)

(58) Field of Classification Search
CPC ........... A61B 2017/00367; A61B 2017/00371; A61B 2017/00389; A61B 2017/00393;
(Continued)

(56) References Cited

U.S. PATENT DOCUMENTS 9,386,970 B2   7/2016 Hermle
10,130,414 B2  11/2018 Weiler et al.
(Continued)

FOREIGN PATENT DOCUMENTS

CN   104271061 A   1/2015
CN   106175923 A   12/2016
(Continued)

OTHER PUBLICATIONS

European Search Report dated Mar. 8, 2019, in corresponding European Application No. 18191442.5 (9 pages).
(Continued)

*Primary Examiner* — Ronald Hupczey, Jr.
*Assistant Examiner* — Bradford C. Blaise
(74) *Attorney, Agent, or Firm* — Fitch, Even, Tabin & Flannery LLP

(57) ABSTRACT

A medical instrument comprising a device for activating or deactivating a function of the instrument. The device comprises first and second parts, which are each movable into an operative position relative to the other part to activate or deactivate a function of the instrument. A second control element for moving the second part into the operative position provides a control portion and comprises, for moving the first part into the operative position, a first control element which provides an additional control portion. The first control element can be moved in an opposite direction the direction from the second control element. Accordingly, the function is activated by moving a control element in a distal direction, and by moving another control element in a proximal direction. A deflection of force by one actuating element for actuating the first part or the second part in the opposite direction is not necessary.

9 Claims, 2 Drawing Sheets

(51) Int. Cl.
*A61B 17/00* (2006.01)
*A61B 18/00* (2006.01)

(52) U.S. Cl.
CPC ............... *A61B 2017/00371* (2013.01); *A61B 2018/0063* (2013.01); *A61B 2018/0091* (2013.01); *A61B 2018/0094* (2013.01); *A61B 2018/00607* (2013.01); *A61B 2018/00916* (2013.01); *A61B 2018/00922* (2013.01); *A61B 2018/00946* (2013.01); *A61B 2018/00952* (2013.01); *A61B 2018/00958* (2013.01); *A61B 2018/1452* (2013.01); *A61B 2018/1467* (2013.01)

(58) Field of Classification Search
CPC ............ A61B 17/2841; A61B 17/2909; A61B 17/320092; A61B 2017/320093; A61B 2017/320094; A61B 2017/320095; A61B 2018/0053; A61B 2018/00577; A61B 2018/00607; A61B 2018/0063; A61B 2018/00636; A61B 2018/00708; A61B 2018/0091; A61B 2018/00916; A61B 2018/00922; A61B 2018/0094; A61B 2018/00946; A61B 2018/00952; A61B 2018/00958; A61B 18/1442; A61B 18/1445; A61B 2018/1452; A61B 2018/1467
See application file for complete search history.

(56) References Cited

U.S. PATENT DOCUMENTS

| | | |
|---|---|---|
| 2007/0043352 A1 | 2/2007 | Garrison et al. |
| 2009/0157074 A1* | 6/2009 | Livneh ............... A61B 18/1445 606/37 |
| 2014/0081455 A1 | 3/2014 | Goldberg et al. |
| 2015/0374430 A1 | 12/2015 | Weiler et al. |
| 2017/0150950 A1 | 6/2017 | Thouément et al. |
| 2017/0150982 A1 | 6/2017 | Stefan et al. |
| 2017/0333118 A1 | 11/2017 | Ellman |

FOREIGN PATENT DOCUMENTS

| | | |
|---|---|---|
| EP | 2156802 A2 | 2/2010 |
| EP | 2792305 A1 | 10/2014 |
| EP | 2959854 A1 | 12/2015 |
| RU | 2015124783 A | 1/2017 |
| WO | 2017/190304 A1 | 11/2017 |

OTHER PUBLICATIONS

Office Action and Search Report dated Jul. 26, 2022 for RU Patent Application No. 2019126317; 11 pages.
Translation of relevant parts of Office Action and Search Report dated Jul. 26, 2022 for RU Patent Application No. 2019126317, 5 pages.
Office Action and Search Report dated Jul. 1, 2022 for CN Patent Application No. 201910807900.X; 12 pages.

* cited by examiner

MEDICAL INSTRUMENT

RELATED APPLICATION(S)

This application claims the benefit of European Patent Application No. 18191442.5, filed Aug. 29, 2018, the contents of which are incorporated herein by reference as if fully rewritten herein.

TECHNICAL FIELD

The invention relates to a medical instrument.

BACKGROUND

Publication EP 2 959 854 A1 discloses a surgical instrument comprising two branches between which tissue can be grasped and comprising cutting and sealing electrodes with which the grasped tissue can be cut and sealed.

The object of the present invention is to state an improved concept for activating or deactivating functions of a medical instrument.

SUMMARY

This object has been achieved with a medical instrument as described herein.

The medical instrument according to the invention comprises a housing and a device for activating or deactivating at least one function of the medical instrument. The device may be referred to as a control or switching arrangement. The arrangement has a first part and a second part that are movable relative to the housing, wherein the second part is arranged and disposed to be moved into an operative position relative to the first part and, in so doing, relative to the housing, in order to thus activate or deactivate the at least one function of the medical instrument. In the operative position, the second part and the first part act together in order to activate or deactivate the at least one function. The at least one function may be, for example, the application of electrical power to electrodes of the medical instrument, in particular an RF power, if the medical instrument comprises electrodes for sealing and/or cutting tissue. Conversely, the first part is arranged and disposed to be moved into an operative position relative to the second part and, in so doing, be moved relative to the housing in order to thus activate or deactivate the at least one function of the medical instrument. Also in this situation, the first part and the second part act together in order to activate or deactivate the at least one function of the medical instrument. Preferably, the respectively other part need not necessarily be moved in order to activate or deactivate the at least one function but, rather, the respectively other part may remain in inoperative position. The medical instrument is preferably a surgical instrument, particularly preferably an RF surgical instrument, with which RF energy can be used, for example, to perform one or more functions, i.e., "cutting", "sealing", "devitalizing" and/or "coagulating".

With the use of the medical instrument according to the invention it is possible to trigger a specific function by the selective control of a control portion, by means of which the second part is moved into the operative position relative to the first part, and an additional control portion, by means of which the first part is moved. The control portion is preferably separate from the additional control portion, for example a separate control element. The control portion and the additional control portion that is disposed for the control of the second part and the first part, respectively, are preferably arranged on the housing. The control portion and the additional control portion may be buttons or levers that are elements not integral to the housing, or the control portion and the additional control portion may be sections of the housing, for example. The control portion for moving the second part into the operative position relative to the first part is preferably disposed to be moved for moving the first part relative to the housing. The additional control portion for moving the first part into the operative position relative to the second part is preferably disposed for moving the first part relative to the housing. For example, only one button is needed for triggering the function selectively with a control portion or an additional control portion. Referring to exemplary embodiments, an element for pressing can be pushed, for example by means of the control portion, against the button for triggering the same function, on the one hand, and the button can be moved by means of the additional control portion against the element for pressing the button, on the other hand. Compared with a solution using two buttons, the solution according to the invention requires less space. In addition, electrical contacting is simplified. In particular, cabling can be simplified. The otherwise required additional cables, for example for an additional button, would imply the risk of impairing movable parts, e.g., mechanical handle components, to the extent that they exist, and would lead to increased development expenses for mounting them safely. Compared to a solution using two buttons, it is possible with the solution according to the invention to save costs for additional components such as push buttons, boards, cables, fixation and additional assembly steps in order to achieve low manufacturing costs.

The medical instrument according to the invention can be advantageously developed with one or more of the features described hereinafter or in accordance with one or more of the embodiments described hereinafter:

The medical instrument may comprise a circuit board on which is provided the first part or the second part, in which case the circuit board is movably held in the medical instrument. In particular, the circuit board can be movably held in a housing of the medical instrument, in particular in a handle housing. In particular, the circuit board may be held or supported in a pivotable and/or tiltable and/or hinged manner.

The first part or the second part can be arranged on the circuit board, the circuit board being a one-sided printed circuit board. Apart from the electrical lines, the other side of the circuit board may be free of components such as, for example, push buttons. Compared to a two-sided printed circuit board, the circuit board can be manufactured at low manufacturing cost. The circuit board may at least comprise a push button on one side only, said push button being the first or the second part.

Referring to other embodiments, the two sides of the circuit board may be equipped with components, in which case, in these embodiments, however, only one side of the circuit board is loaded with a push button. Preferably, the button is the first part.

The second part can be mounted to one control portion, for example a control element, that is movably supported. Alternatively or additionally, the first part can be mounted to an additional control portion, for example an additional control element, that is movably supported. A separate movable support of the first part and/or a separate movable support of the second part may thus be omitted.

Referring to the embodiments of the medical instrument, the medical instrument comprises a control portion for controlling the second part, in particular for moving the second part into the operative position relative to the first part, in which case, based on the control of the control portion, an additional function of the medical instrument is performed. The additional function of the medical instrument may, for example, be a mechanical action on the tissue, for example, a grasping of tissue between two branches. The control portion may be coupled strictly mechanically with the tool of the medical instrument for performing the additional function.

Preferably, the control portion can be controlled in such a manner that the additional function is performed, without the function being activated or deactivated due to the control of the control portion, in particular the movement of the control portion. The medical instrument may be set up in such a manner that the control portion can be moved by the user, in which case, due to a first section of movement, the additional function is performed and, only due to an additional subsequent section of movement, the function is activated or deactivated.

Preferably, the medical instrument is disposed to convey to the user, by means of a haptic feedback, that if the control portion is continued to be moved, the at least one function is activated or deactivated. The feedback can be perceived by the user, e.g., perceived acoustically or visually, or manually. Preferably, the feedback can be felt with the hand that is used by the user to control the instrument.

Preferably, the medical instrument comprises an additional control portion for controlling the first part, in particular for moving the first part into the operative position relative to the second part. Particularly preferably, the control of the additional control portion does not trigger the execution of an additional function of the medical instrument.

A particularly simple setup is obtained when the additional control portion is a section of an element which is a support of the first part or a circuit board that comprises the first part. The element or the support, respectively, is preferably kept movable, in particular movably supported, for example pivotally supported.

The medical instrument becomes particularly easy to control when the control portion can be moved in proximal direction for activating or deactivating the function and/or for triggering the additional function, and, when the additional control portion can be moved in distal direction in order to activate or deactivate the function. Alternatively, this would also be possible, for example, when the control portion can be moved in distal direction in order to activate or deactivate the function and/or in order to trigger the additional function, and when the additional control portion can be moved in proximal direction in order to activate or deactivate the function. The control portion and the additional control portion are preferably arranged on different sides of the instrument, in particular arranged on different sides of a handle of the instrument, and/or face in different directions, for example the distal direction and the proximal direction. The distal end of the instrument may comprise a working portion with at least one tool that can perform the at least one function. The control portion can preferably be moved away from the working portion of the instrument in order to activate or deactivate the function and/or the additional function.

Referring to preferred embodiments, the control portion for controlling the second part is a portion of an element that can be moved relative to the element that holds the second part. During operation, the element whose portion is the control portion for controlling the second part can be displaced against the element that comprises the second part in order to move the second part into the operative position relative to the first part, in particular displace the second part against the first part. In so doing, it can be accomplished that the movement of the control portion is still disposed for activating an additional function, for which one other or additional control movement is necessary than for controlling the second part. Of course, it is possible for at least one more movably held intermediate element to be present between the element whose portion is the control portion and the element that holds the second part, said intermediate element being displaced against the element holding the second part by means of the element whose portion is the control portion, in order to move the second part into the operative position relative to the first part.

Preferably, the medical instrument comprises an additional device for activating one of the functions of the at least one function. This additional device can preferably be controlled by an additional control portion. Referring to the exemplary embodiments, the functions "sealing" and "cutting" can be activated, for example, by means of the device, and only the function "sealing" can be activated by means of the additional device. For example, the device may comprise a button for activating both the function "sealing" as well as the function "cutting", and the additional device may comprise an additional button for activating only the function "sealing".

The control portion for moving the second part into the operative position relative to the first part is preferably elastically coupled with a tool for performing the additional function of the medical instrument.

BRIEF DESCRIPTION OF THE DRAWINGS

Additional advantageous embodiments and preferred features can be inferred from the dependent claims, as well as from the description hereinafter and the figures. They show in FIG. 1—a schematic perspective overall display of an exemplary embodiment of an instrument according to the invention;

DETAILED DESCRIPTION

Figure 1:
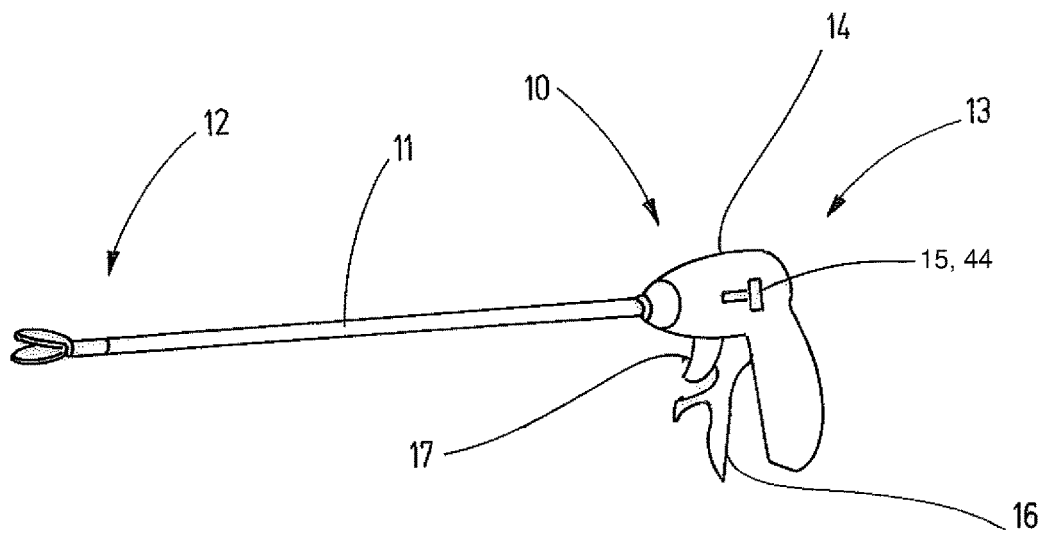
Figure 2:
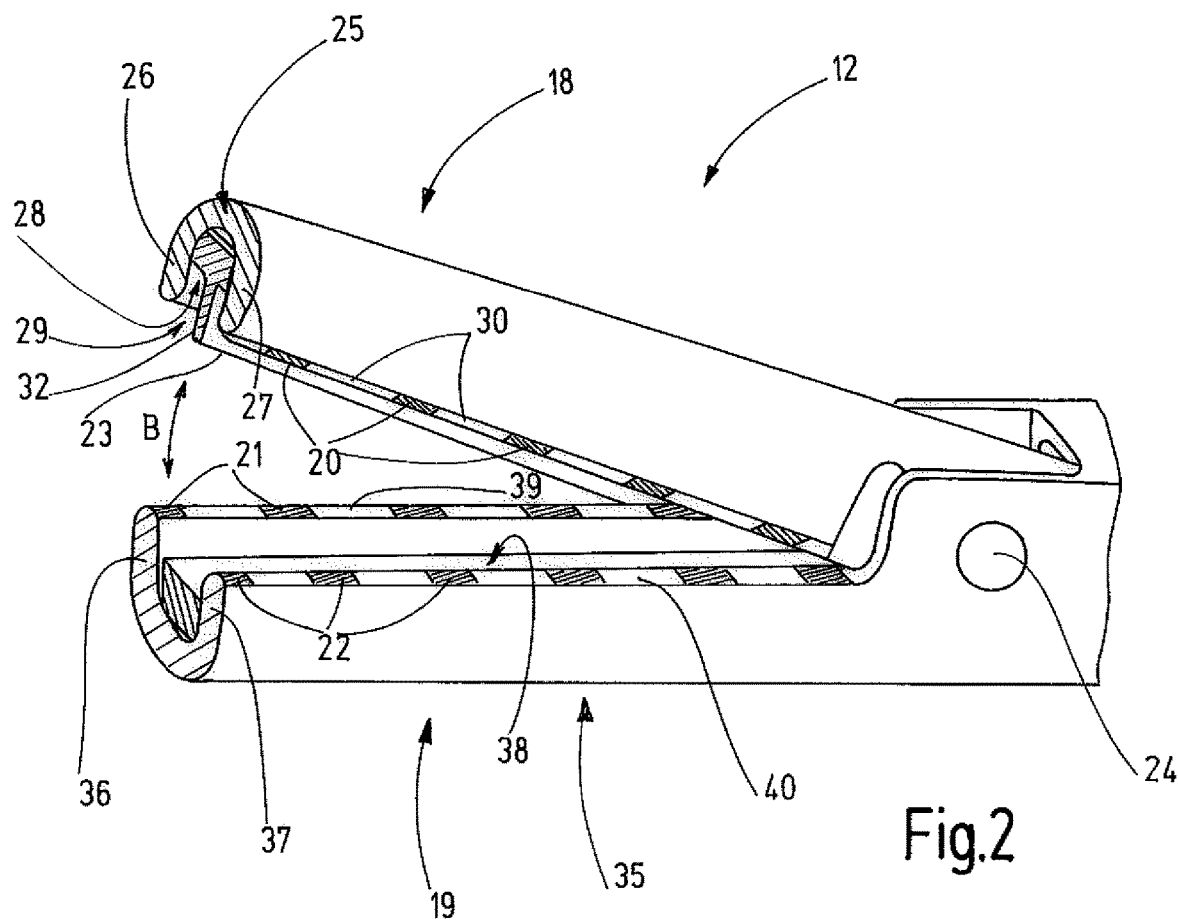
FIG. 2—an enlarged perspective representation, partially in section, of the distal portion of the medical instrument according to FIG. 1 with the group of tools.
Figure 3:
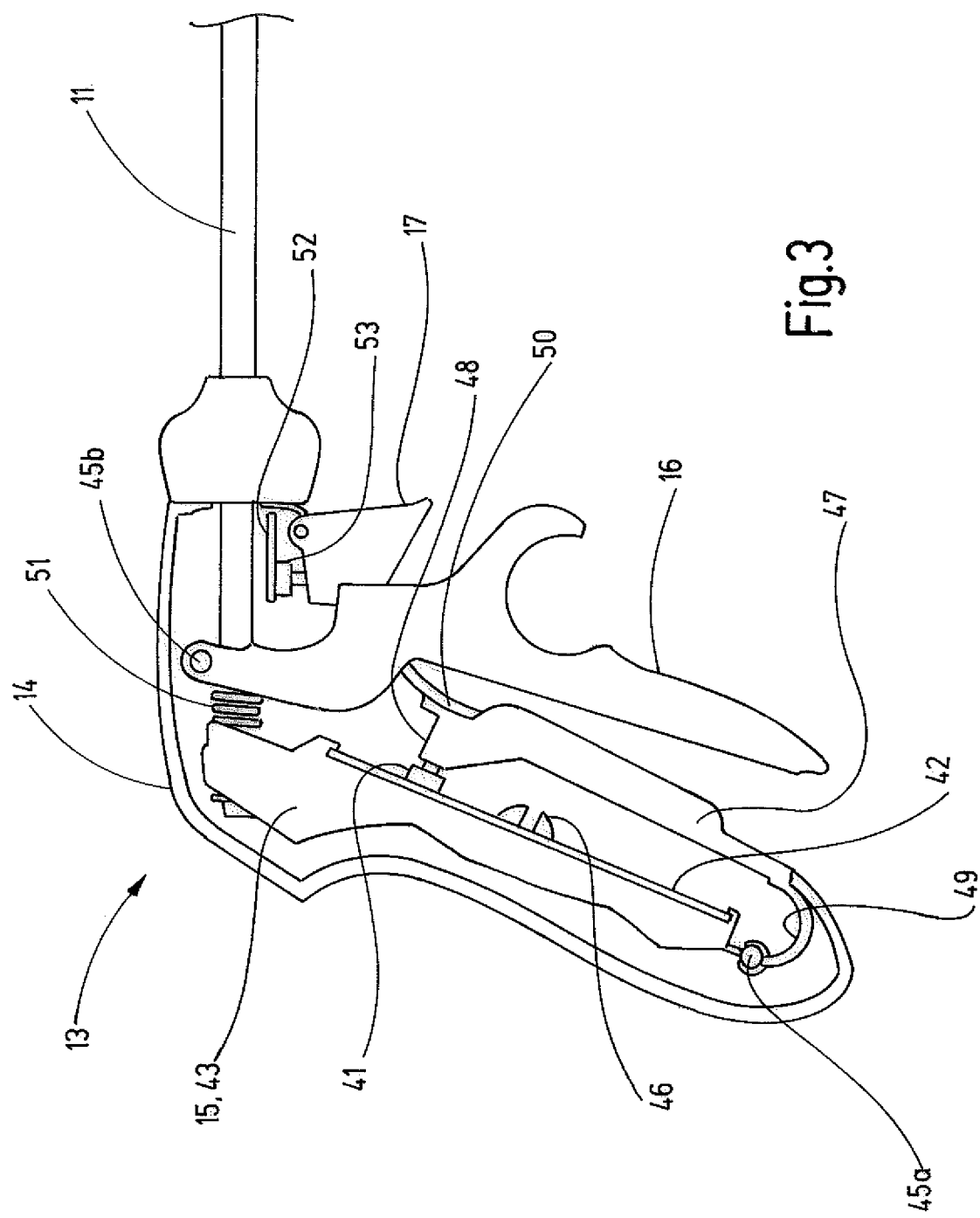
FIG. 3—a lateral view into the half-opened housing of the handle of the exemplary medical instrument according to FIG. 1.

In particular, the medical instrument according to the invention may be surgical instrument 10, for example one such as shown schematically and in an exemplary manner by FIGS. 1, 2 and 3. The medical instrument 10 shown by FIGS. 1, 2 and 3 comprises the functions of "grasping tissue", "cutting" and "sealing" of tissue and may be referred to as a sealing instrument. Accordingly, the group 12 of tools of the instrument is disposed for sealing and, optionally, for severing tissue, in which case the vessels and lumens contained in the tissue are closed at the tissue seam and should thus be sealed. Although the invention is described hereinafter with reference to a sealing instrument 10, it is possible according to the invention to further develop also other medical instruments that do not display the said functions and/or display other functions.

The medical instrument 10 according to the invention as represented in an exemplary manner by FIG. 1 may have an elongated shaft 11 that bears a group 12 of tools on the distal end. On the proximal end, the shaft 11 is connected to a handle part 13 which has a housing 14. The instrument 10 comprises control elements 15, 16, 17 (These may also be referred to as actuating elements.) for controlling the tools of group 12. The medical instrument 10 according to the invention comprises, for example, a first control element 15, a second control element 16 and a third control element 17, which may be arranged on the handle part 13 as represented (FIGS. 1 and 3). The tools of group 12 for performing the functions may be embodied as illustrated for example by FIG. 2. The depicted exemplary medical instrument 10 comprises a tool for grasping tissue by means of two branches 18, 19, whereby at least one of these is movably supported. As an additional tool, each branch supports electrodes 20 and 21, 22, respectively, for sealing tissue, and one branch supports an electrode 23 for cutting tissue.

The tool with the branches 18, 19 for grasping the tissue, as well as the electrodes 20, 21, 22, 23 for cutting and sealing the grasped tissue may be configured and may operate, for example, as explained in publication EP 2 959 854 A1.

At least one of the branches 18, 19 of the tool for grasping tissue provided on the instrument 10 is supported so as to be pivotable about the pivot axis 24. In FIG. 2 this is the upper branch 18. In so doing, it is possible, depending on the application, to support the first branch 18 or the second branch 19 or both branches 18, 19 so as to be pivotable about a joint pivot axis or about separate pivot axes or be movable in another manner, so that the branches 18, 19 can be moved toward each other and away from each other.

The first branch 18 comprises a base body 25 having a cross-section in the form of a U-profile. The base body 25 comprises two sealing jaws 26, 27 that are parallel to each other, are electrically preferably connected to each other and delimit a groove 28 between each other. Preferably, this groove extends over the greatest part of the length of the branch 18 and is disposed to accept a cutting electrode support 29. The groove 28 is delimited by the edges of the sealing jaws 26, 27, where the sealing electrodes 20 are formed. Based on the illustration of FIG. 2, only the sealing electrodes of the one first sealing jaws 27 are visible. The sealing electrodes 20 can be connected to the base body 25 in an electrically conductive manner. As can be inferred from FIG. 2, the sealing electrodes 20 of the two first sealing jaws 26, 27 preferably form a series of spaced apart individual conductive surfaces that are separated from each other by insulating regions 30.

The cutting electrode support 29 comprises a cutting electrode 23 that is arranged on said support's face side. In so doing, the cutting electrode 23 is seated in a groove or recess of the wall-like extension 32 of the cutting electrode support 29. One face of the cutting electrode 23 is exposed.

The length of the wall-like extension 32—measured from the foot to the cutting electrode 23—is preferably such that the exposed face of the cutting electrode 23 facing the second branch 19 projects beyond the sealing jaws 26, 27.

The second branch 19 also has a base body 35, preferably of electrically conductive material. Again, the base body 35 has a U-shaped cross-section, wherein a groove 38 is formed between two sealing jaws 36, 37. The sealing electrodes 21, 22 are arranged between the insulating regions 39, 40 on the second sealing jaws 36, 38 of the second branch 19, said jaws preferably being electrically connected.

The first control element 15 in the depicted exemplary embodiment is a button (thumb button) or lever laterally projecting from the housing 14 of the handle part 13, wherein said button or lever it to be actuated with the thumb, in which case the first control element 15 is to be pushed from the proximal location in distal direction and, in so doing, to be moved relative to the housing 14 in order to apply electrical power to an electrode—in the depicted exemplary instrument according to the invention, the electrode for cutting 23 and sealing 20, 21, 22—in order to use them to cut and seal tissue. The second control element 16 in the depicted instrument 10 according to the invention is arranged on the underside of the housing 14 of the handle part 13 and is a lever that is to be actuated with the fingers, said lever being supported by the housing in a pivotable manner by means of the swivel bearing 45b. For example, the lever 16 is mechanically coupled with a tool of the medical instrument in order to mechanically transmit a manual force to the corresponding tool. In the depicted exemplary embodiment, the lever 16 is mechanically coupled, for example, with the at least one pivotally movable branch 18 in order to close the branches 18, 19 for grasping tissue, in that the lever 16 is moved in proximal direction. By means of the second control element 16, it is possible to furthermore trigger the same functions that can also be triggered with the first control element 15, as will be described in detail hereinafter. The third control element 17 which the medical instrument 10 may have is a button or lever arranged in the depicted exemplary embodiment in front of the second control element, said button or lever being controlled with the forefinger. When the third control element 17 is moved back in proximal direction with the forefinger, preferably one of the functions, which can be triggered by actuating the first control element 15 or by actuating the second control element 16, is triggered. For example, by actuating the third control element 17, the function, "sealing" can be triggered by applying electrical power to the sealing electrodes 20, 21, 22, while the cutting electrode 23 is not coupled with the third control element 17 in such a manner that, by actuating the third control element 17, the cutting electrode 23 would be charged with electrical power.

FIG. 3 shows a detail of a lateral view of the exemplary embodiment of the instrument 10 according to the invention as in FIG. 1 (the distal working portion of the instrument 10 with the group 12 of tools is not shown), in which the interior of the housing 14 can be seen through the laterally opened housing 14. The instrument 10 comprises an activating device for activating the functions "cutting" and "sealing", which comprise as the first portion, a button 41 that is supported by a circuit board 42 (printed board). The button 41 is connected to a (not illustrated) control for the application of an RF power to the electrodes 20, 21, 22, 23 for "cutting" and, "sealing", so that—with the appropriate switch condition of the contacts of the button 41—electrical power is applied to the corresponding electrodes 20, 21, 22, 23.

Preferably, the circuit board 42 is provided only on one side with electrical components; in particular, a button 41 is arranged only on one side of the board 42. Preferably, the board 42 is mounted to the first control element 15. The first control element 15 has a holding portion 43 located inside the housing 14 and a control portion 44 located outside the housing (see FIG. 1). The first control element 15 is held movably; in particular, it is pivotally movable, in the housing 14. The first control element 15 in the exemplary embodiment is pivotally supported in the housing 14 by a swivel bearing 45a connected to the housing 14. In the depicted embodiment the board 42 is mounted to the first control element 15, for example by means of a snap-catch portion 46 that comes into engagement with an opening (not illustrated) in the board 42. Consequently, the circuit board 42 is movably supported in the housing 14 by means of the first control element 15. A movement of the first control element 15 in proximal direction may be delimited by an abutment portion (not illustrated). The abutment portion may be mounted or molded to the housing 14, for example. The first control element 15 may be resiliently biased in proximal direction against the abutment portion. FIG. 3 shows the first control element 15 in its inactivated inoperative position.

Opposite the board 42 and the button 41, there is arranged a holding element 47 which has a second part 48. The second part 48 is the actuating portion 48 of the holding element 47. The holding element 47 is held in the housing 14 so as to be movable. To do so, the holding element 47 comprises a resilient portion 49 which is connected to the housing 14 at the same point where also the first control element 15 is connected to the housing 14. The holding element 47 is set up and arranged such that the second part 48 can be moved into an operative position relative to the button 41. In the depicted embodiment, the second part 48 can be displaced against the button 41 in order to open or close an electrical contact of the button 41 in order to activate cutting by means of the cutting electrode 23 and sealing by means of the sealing electrodes 20, 21, 22. Displacing the second part 48 against the first part 41 is accomplished by moving the second control element 16 in proximal direction, said element being displaced against the holding element 47, which may project from the housing 14 in its inoperative position (as shown by FIG. 3), in that said holding element projects beyond the contour of the housing. The movement of the holding element 47 in distal direction can be limited by an abutment portion 50 which may be fastened or molded to the housing 14. In its inoperative position, the holding element 47 may be held resiliently pretensioned against the abutment portion 50.

The second control element 16 and the holding element 47 are—as illustrated—preferably elements that are separate from each other. The second control element 16 is arranged in such a manner—in particular at a distance from the holding element 47—that the control of the second control element 16 out of the distal inoperative position (the second control element 16 can be pretensioned against an abutment therein, e.g., by means of a pressure spring, as described hereinafter) into the proximal position initially leads to a closing movement of the movable branch 18, without activating the functions "cutting" and "sealing", and leads—only during the continued progress of movement of the second control element 16—to the actuation of the functions "cutting" and "sealing" by actuating the button 41 via the holding element 47.

The instrument 10 according to the invention may be set up to provide the user, while operating the second control element 16, with a feedback that can be manually felt, indicating that, with continued movement of the second control element 16, an activation of the function, "cutting" and, "sealing" will take place. This can be accomplished, for example, by means of a device (not illustrated) that has the effect that the user, for moving the second control element 16 in the direction toward the holding element 47, must apply noticeably more force by hand in a specific position of the second control element 16 in order to move the second control element 16 further in the direction toward the holding element 47 and in proximal direction, respectively.

The second control element 16 is coupled—with a tool of the medical instrument—for example the pivotable branch 18 of the depicted instrument 10 according to the invention—not in a rigid manner but in a mechanically elastic manner, in particular by means of a spring element such as, for example, a pressure spring 51, in order to transmit the force to the tool, for example for actuating the branch 18. The elastic coupling, for example the spring element 51, is disposed and designed to substantially determine the stiffness of the transmission path for transmission of the manual force to the at least one pivotally movable branch. The spring element 51 is distinguished in that it displays a smaller spring constant than the other transmission members for the transmission of the movement of the second control element 16 to the tool and is biased to such an extent that the desired clamping force between the branches 18, 19 is achieved before deformation occurs. The movement of the second control element 16 is converted into a proximal movement of the spring element 51, which, in turn, is converted into a movement of the tool, for example the branch 18. The elastic deformation of the spring element 51 after it has reached the desired clamping force can be achieved, for example, by means of a pull and/or push rod displaying pulling and/or pushing rigidity. This leads to a force limitation or to a limitation of the transmission of force by the second control element 16 to the tool. Conversely, the mechanically elastic coupling causes the tool to uncouple from the control element 16 to the extent that the control element 16 can be brought into the position for activating or deactivating the function by actuating the button 41 via the holding element 47 when the movement of the tool, for example the branch 18, is impaired beyond a certain position, for example by tissue that is being grasped between the branches 18, 19, so that the branches 18, 19 can no longer be closed further when the second control element 16 is actuated. Due to the elastic coupling, it is possible, however, to move the control element 16 under elastic deformation of the spring element 51 into the position for activating or deactivating the functions "cutting" and "sealing".

According to the invention, the user has another option for activating the functions "sealing" and "cutting". This is because the first part 41, i.e., the button 41, can be displaced by means of the first control element 15 against the second part 48—in the example against the actuating portion of the holding element 47. In so doing, the first part 41 is moved into an operative position relative to the second part 48, i.e., in a direction which is opposite the direction of movement of the second part 48 for moving the second part 48 into an operative position relative to the first part 41. When the first part 41 is displaced by means of the first control element 15 against the second part 48, the holding element 47 abuts against the abutment portion 50. Whereas in the depicted exemplary embodiment a mechanical contact of the first part 41 and the second part 48 is necessary so that the button 41 connects or disconnects an electrical contact, the first part 41 may also be a capacitive sensor or an inductive sensor, for example, so that it is only necessary that the second part 48 be moved into a specific position (operative position) relative to the first part 41, or that the first part 41 be moved into a specific position (operative position) relative to the second part 48, in order to trigger the connection or disconnection of an electrical connection for activating or deactivating the first part 41 in a capacitive or inductive manner, for example, without necessarily requiring an application of force by the second part 48 on the first part 41 or the first part 41 on the second part 48, so that the first part 41 establishes or terminates the electrical connection.

The instrument 10 preferably comprises another activating device that can activated with one of the functions, e.g., "sealing", which functions can be activated by means of the first and the second control elements 15, 16. Preferably an activation of the at least one function (e.g., "cutting) which can be activated by controlling the first control element 15 is not possible by means of the additional activating device. The additional activating device, for example, may comprise—as illustrated—an additional circuit board 52 with an additional button 53, in which case the third control element 17 can be moved by moving the third control element 17 in proximal direction in operative position relative to the additional button 53 in order to push the additional button 53, so that the additional button 53 thus triggers the function.

The medical instrument 10 according to the invention operates as follows:

For sealing and severing of tissue, in particular hollow vessels or tissue containing hollow vessels, said tissue is to be grasped between the branches 18, 19. By appropriately activating the second control element 16 the movable branch 18 is moved toward the other branch 19 in such a manner that biological tissue is grasped between the branches 18, 19. To do so, the user pulls the lever 16 that is the second control element 16 toward him/herself, i.e., in proximal direction. The instrument 10 can give the user a feedback that can be felt by the hand with which the user holds the instrument 10, namely, that with continued pulling back of the lever 16, an activation of the functions "sealing" and "cutting" occurs. For sealing the tissue, an electrical voltage, preferably a high-frequency AC voltage becomes effective between the branches 18, 19, so that, between the electrodes 20 of the first branch 18 and the electrodes 21, 22 of the second branch 19, an electrical current flows through the biological tissue in order to heat it and bring about a fusion of the grasped tissue. At the same time, the cutting electrode 23 is being activated. The latter is also supplied with an electrical voltage, for example an RF voltage, having a reference potential at one of the branches 18, 19, preferably the second branch 19, i.e., the sealing electrode 21, 22. The current density on the face of the cutting electrode 23 is high enough for the biological tissue to be cut smoothly.

It is also possible for the user to supply the electrodes 23, 20, 21, 22 for cutting and sealing with an RF power, without pulling the lever 16 that represents the second control element 16 in proximal direction, in that the user pushes the first control element 15. Thus a cutting of tissue and/or a coagulation could also take place with open branches 18, 19, e.g., for cutting large vessels. It is also possible to supply the electrodes 23, 20, 21, 22 for cutting and for sealing by means of the first control element 15 with RF power when the branches 18, 19 are partially closed and the second control element 16 is in one position, so that the holding element 47 is not yet pushed in an actuating manner against the button 41 due to the distance between the holding element 48 and the second control element 16.

In addition, with the branches 18, 19 open or partially closed, the user can activate sealing by means of the third control element 17 which, when activated, acts on the additional button 53.

According to the invention a medical instrument 10 is disclosed, said instrument comprising a device for activating or deactivating a function of the medical instrument. The device comprises a first part 41 and a second part 48, in which case the second part 48 is arranged and set up to be moved into an operative position relative to the first part 41 in order to thus activate or deactivate at least one function of the medical instrument 10, and in which case the first part 41 is arranged and set up to be moved into an operative position relative to the second part 48 in order to thus activate or deactivate the at least one function of the medical instrument 10. The medical instrument 10 comprises, for moving the second part 48 into the operative position, preferably a second control element 16, which provides a control portion and comprises, for moving the first part 41 into the operative position, preferably a first control element 15 which provides an additional control portion. For activating the function, the first control element 15 can preferably be moved in a direction that is opposite the direction, in which the second control element 16 for activating the function can be moved. As a result of this, the function can be activated, for example by moving a control element 15 from the back to the front, i.e., in distal direction, and by moving another control element 16 in opposite direction from the front to the back, i.e., in proximal direction. A deflection of force by one actuating element 15, 16 for actuating the first part or the second part in opposite direction is therefore not absolutely necessary.

LIST OF REFERENCE SIGNS

| | |
|---|---|
| 10 | Instrument |
| 11 | Shaft |
| 12 | Group of tools |
| 13 | Handle part |
| 14 | Housing |
| 15 | First control element |
| 16 | Second control element |
| 17 | Third control element |
| 18 | First Branch |
| 19 | Second Branch |
| 20, 21, 22 | Sealing electrode |
| 23 | Cutting electrode |
| 24 | Pivot axis |
| 25 | Base body |
| 26 | Sealing jaw |
| 27 | Sealing jaw |
| 28 | Groove |
| 29 | Cutting electrode support |
| 30 | Insulating regions |
| 32 | Extension |
| 35 | Base body |
| 36 | Sealing jaw |
| 37 | Sealing jaw |
| 38 | Groove |
| 39 | Insulating region |
| 40 | Insulating region |
| 41 | First part/push button |
| 42 | Board/ circuit board |
| 43 | Holding portion |
| 44 | Control portion |
| 45a | Swivel bearing |
| 45b | Swivel bearing |
| 46 | Snap-catch portion |
| 47 | Holding element |
| 48 | Second part/actuating portion |
| 49 | Resilient portion |
| 50 | Abutment portion |
| 51 | Pressure spring |
| 52 | Additional circuit board |
| 53 | Additional push button |

The invention claimed is:
1. A medical instrument (10), comprising:
a housing (14); and
a device for activating or deactivating at least one function of the medical instrument, wherein the device comprises a first part (41) and a second part (48);
wherein the second part (48) is configured to be moved into an operative position relative to the first part (41) and to the housing (14) to activate or deactivate the at least one function of the medical instrument (10);

wherein the first part (41) is configured to be moved into an operative position relative to the second part (48) and to the housing (14) to activate or deactivate the at least one function of the medical instrument (10);

wherein the first part (41) includes a button mounted to a side of a circuit board (42), wherein actuation of the button activates or deactivates the at least one function of the medical instrument (10), wherein the circuit board (42) is held in a movable manner by a control element (15) that is movably supported within the housing (14); and an additional control portion (44) configured to move the circuit board (42) and the button mounted thereto into the operative position relative to the second part (48), wherein control of the additional control portion (44) does not trigger the performance of another function of the medical instrument (10) and the additional control portion (44) is a portion of the control element (15).

2. The medical instrument (10) according to claim 1, further comprising a control portion (16) configured to move the second part (48) into the operative position relative to the first part (41), wherein, based on control provided by the control portion (16), an additional function of the medical instrument (10) is performed.

3. The medical instrument (10) according to claim 2, wherein the control portion (16) is configured to be controlled, so that the additional function is performed without the at least one function being activated or deactivated.

4. The medical instrument (10) according to claim 3, wherein the medical instrument (10) is configured to convey to a user after an initial movement of the control portion (16) that in the event of further movement of the control portion (16) the at least one function is activated or deactivated.

5. The medical instrument (10) according to claim 2, wherein the control portion (16) is configured to be moved in a proximal direction in order to activate or deactivate the at least one function and/or in order to trigger the additional function, and wherein moving the additional control portion (44) in a distal direction activates or deactivates the at least one function.

6. The medical instrument (10) according to claim 2, wherein the control portion (16) for controlling the second part (48) is configured to be moved relative to an element (47) which comprises the second part (48).

7. The medical instrument (10) according to claim 2, wherein the control portion (16) that is disposed for moving the second part (48) into the operative position relative to the first part (41) is mechanically elastically coupled with a tool (18) for performing the additional function of the medical instrument (10).

8. The medical instrument (10) according to claim 1, wherein the at least one function comprises two functions that are different from one another, and the medical instrument (10) further comprising an additional device (53, 17) configured to activate only one of the two functions.

9. The medical instrument of claim 1, wherein the second part (48) is mounted to a second control element that is movably supported.

* * * * *